(12) United States Patent
Bundred

(10) Patent No.: US 7,553,815 B1
(45) Date of Patent: Jun. 30, 2009

(54) THERAPEUTIC USE

(75) Inventor: Nigel James Bundred, Cheshire (GB)

(73) Assignee: The University of Manchester, Manchester (GB)

( * ) Notice: Subject to any disclaimer, the term of this patent is extended or adjusted under 35 U.S.C. 154(b) by 306 days.

(21) Appl. No.: 10/111,390

(22) PCT Filed: Nov. 1, 2000

(86) PCT No.: PCT/GB00/04190

§ 371 (c)(1),
(2), (4) Date: Aug. 9, 2002

(87) PCT Pub. No.: WO01/32155

PCT Pub. Date: May 10, 2001

(30) Foreign Application Priority Data

Nov. 2, 1999 (GB) ................................. 9925958.2

(51) Int. Cl.
*A61K 31/535* (2006.01)
(52) U.S. Cl. .................... 514/15; 514/228.8; 514/234.5; 514/253.01; 514/259.1
(58) Field of Classification Search .............. 514/228.8, 514/234.5, 253.01, 259.1, 15
See application file for complete search history.

(56) References Cited

U.S. PATENT DOCUMENTS 5,770,599 A * 6/1998 Gibson ..................... 514/228.2

FOREIGN PATENT DOCUMENTS

| EP | 0 566 266 | 10/1993 |
|---|---|---|
| WO | WO 96/30347 | 10/1996 |
| WO | 97 02266 | 1/1997 |
| WO | WO 2008/026150 | 3/2005 |

OTHER PUBLICATIONS van Agthoven et al. (Amer. J. Path. 1994; 144: 1238-1246).*
Granziero et al. (Eur. J. Immunol. 1999, 29:1127-1138).*
Byers, T. (CA Journal, vol. 49, No. 6, Nov./Dec. 1999).*
Kelloff et al. (Cancer Epidemiology, Biomarkers & Prevention 1996; 5: 657-666).*
Smaill et al. (J. Med. Chem. 1999; 42: 1803-1815).*
Bruns et al. (Cancer Research 2000; 60: 2926-2935).*
Fisher (CA Cancer J. Clin. 1999; 49: 159-177).*
Levitt et al. (Investigational New Drugs 1999; 17: 213-226, published Aug. 1999).*
Stanta et al. (Virchows Arch 1998; 432: 107-111).*
Driscoll D et al: "Effect of epidermal growth factor receptor tyrosine kinase inhibitor PD183805 on vascular endothelial growth factor secretion from several tumor models." Proceedings of the American Association for Cancer Research Annual, vol. 40, Mar. 1999, p. 121.
Baselga J (Reprint) et al.: "A pharmacokinetic/pharmacodynamic trial of ZD1839 (IRESSA(TM)), a novel oral epidermal growth factor receptor tyrosine kinase (EGFR-TK) inhibitor, in patients with 5 selected tumor types (a phase I/II trial of continuous once-daily treatment)." Clinical Cancer Research, (Nov. 1999) vol. 5, Supp. 'S!, pp. 29-29.
Smaill J.B. et al.: "Tyrosine kinase inhibitors. 15. 4-(Phenylamino)quinazoline and 4-(phenylamino)pyrido'd!pyrimidine acrylamides as irreversible inhibitors of the ATP binding site of the epidermal growth factor receptor." Journal of Medicinal Chemistry, (May 20, 1999) 42/10 (1803-1815).
Ciardiello, Fortunato et al.: "Antitumor effect and potentiation of cytotoxic drugs activity in human cancer cells by ZD—1839 (Iressa), and epidermal growth factor receptor-selective tyrosine kinase inhibitor" Clin. Cancer Res. (2000), 6(5), 2053-2063.
Woodburn J.R.: "The epidermal growth factor receptor and its inhibition in cancer therapy." Pharmacology and Therapeutics, (1999) 82/2 (241-250), XP000965337 p. 241, col. 1, paragraph 1 p. 246, col. 1, paragraph 2.
McKinnon C.: "Prostate cancer, biological therapy, signal transduction inhibitors and anti-angiogenesis agents." IDrugs (1999) 2/7 (624-628). , XP001015291 p. 626, col. 2, paragraph 4.
McKinnon C.: "Epidermal growth factor receptor targeting." IDrugs. (1999) 2/7 (633-635). , XP001015294 p. 633, col. 1, paragraph 5 -col. 2, paragraph 3.
Bridges A.J.: "Current progress towards the development of tyrosine kinase inhibitors as anticancer agents." Emerging Drugs, (1998) 3/- (279-292). , XP001015295 p. 282, paragraph 3 p. 281, paragraph 3.
C. Lu, et al. al, "Effect of Epidermal Growth Factor Receptor Inhibitor on Development of Estrogen Receptor-Negative Mammary Tumors", Journal of the National Cancer Institute, vol. 95, No. 24, Dec. 17, 2003, pp. 1825-1833.
M. Gail, et al., "Projecting Individualized Probabilities of Developing Breast Cancer for White Females Who Are Being Examined Annually", Journal of the National Cancer Institute, vol. 81, No. 24, Dec. 20, 1989, pp. 1879-1886.
G. Boland, "Biological Response to Hormonal Manipulation in Oestrogen Receptor Positive Ductal Carcinoma in situ of the Breast", British Journal of Cancer, vol. 89, 2003, pp. 277-283.
J. Paez, et al., "EGFR Mutations in Lung Cancer: Correlation with Clinical Response to Gefitinib Therapy", Science, vol. 304, Jun. 4, 2004, pp. 1497-1500.
G. Minckwitz, et al., "A Multicentre Phase II Study on Gefitinib in Taxane- and Anthraceycline-pretreated Metastatic Breast Cancer", Breast Cancer Research and Treatment, vol. 89, 2005, pp. 165-172.
J. Soh, et al., "Impact of HER2 and EGFR gene status on Gefitinib-treated Patients wit Nonsmall-cell Lung Cancer", Int. J. Cancer, vol. 121, 2007, pp. 1162-1167.
T. Pugh, et al., "Correlations of EGFR mutations and increases in EGFR and HER2 copy number to gefitinib response in a retrospective analysis of lung cancer patients", BMC Cancer 2007, 7:128.
B. Shoker, et al., "Estrogen Receptor-Positive Proliferating Cells in the Normal and Precancerous Breast", American Journal of Pathology, vol. 155, No. 6, Dec. 1999.

(Continued)

Primary Examiner—Brandon J Fetterolf
(74) Attorney, Agent, or Firm—Swanson & Bratschun, L.L.C.

(57) ABSTRACT

A method of chemoprevention of the onset of invasive breast cancer in a high risk patient comprises administering to the patient an effective amount of an EGFR tyrosine kinase inhibitor.

5 Claims, 2 Drawing Sheets

OTHER PUBLICATIONS

A. Gandhi, et al, "Effects of a Pure Antiestrogen on Apoptosis and Proliferation within Human Breast Ductal Carcinoma in situ1", Cancer Research 60, 4284-4288, Aug. 1, 2000.

N. Anderson, et al., "ZD1839 (Iressa), a novel epidermal growth factor receptor (EGFR) tyroskine inhibitor, potently inhibits the growth of EGFR-positive cancer cell lines with or without erbb2 overexpression", Int. J. Cancer: 94, 774-782 (2001).

V. Rusch, et al., "Differential expression of the epidermal growth factor receptor and its ligands in primary non-small cell lung cancers and adjacent benign lung", Cancer Research 53, 2379-2385, May 15, 1993.

K. Chan, et al., Blockade of growth factor receptors in ductal carcinoma in situ inhibits epithelial proliferation. British Journal of Surgery 2001, 88, 412-418.

K. Chan, et al., Effect of epidermal growth factor receptor tyrosine kinase inhibition on epithelial proliferation in normal and premalignant breast. Cancer Research 62, 122-128, Jan. 1, 2002.

W. Gulick, A new model for ductal carcinoma in situ suggests strategies for treatment. Breast Cancer Research. vol. 4 No. 5.

A. Tan, et al., Evaluation of biologic end points and pharmacokinetics in patients with metastatic breast cancer after treatment with erlotinib, an epidermal growth factor receptor tyrosine kinase inhibitor. Journal of Clinical Oncology. vol. 22, No. 15. Aug. 1, 200.

C. Kari, et al., Targeting the epidermal growth factor receptor in cancer: apoptosis takes center stage1. Cancer Research 63: 1-5, Jan. 1, 2003.

N. Barnes, et al., Absence of HER4 Expression Predicts Recurrent of Ductal Carcinoma In Situ of the Breast. Clinical Cancer Research. vol. 11, 2163-2168, Mar. 15, 2005.

K. Robertson, et al., Quantitative Estimation of Epidermal Growth Factor Receptor and c-erbB-2 in Human Breast Cancer1. Cancer Research 56, 3823-3830, Aug. 15, 1996.

C. Fabian, et al., Prevalence of aneuploidy, overexpressed ER, and overexpressed EGFR in random breast aspirates of women at high and low risk for breast cancer. Breast Cancer Research and Treatment 30: 263-274, 1994.

Pilichowska et al. (1997) "Immunohistochemical Study of TGF-α, TGF-β1, EGFR, and IGF-1 Expression in Human Breast Carcinoma" Mod Pathol 10(10):969-975.

Mourad et al. (1997) "Predictors of Invasion in Ductal Carcinoma in Situ of the Breast: the Value of a Scoring System" Annals of Saudi Medicine 17(4):427-431.

* cited by examiner

Proliferation (Ki67 LI) and apoptosis (AI) in ER-/EGFR+ and ER+/EGFR+ DCIS epithelium.

ZD1839 dose response in (a) DCIS and (b) normal breast

THERAPEUTIC USE

The present invention relates to the therapeutic use of compounds which possess inhibitory activity against the epidermal growth factor receptor (EGFR) tyrosine kinase enzyme. In particular the invention relates to the use of such compounds to inhibit the transformation of normal cells into cancerous cells i.e. the compounds are cancer chemopreventative agents.

In recent years it has been discovered that a cell may become cancerous by virtue of the transformation of a portion of its DNA into an oncogene i.e. a gene which, on activation, leads to the formation of malignant tumour cells (Bradshaw, *Mutagenesis*, 1986, 1, 91). Several such oncogenes give rise to the production of proteins which are receptors for growth factors. The growth factor receptor complex subsequently leads to an increase in cell proliferation. It is known, for example, that several oncogenes encode tyrosine kinase enzymes and that certain growth factor receptors are also tyrosine kinase enzymes (Yarden et al., *Ann. Rev. Biochem.*, 1988, 57, 443; Larsen et al. *Ann. Reports in Med. Chem.* 1989, Chpt. 13).

Receptor tyrosine kinases are important in the transmission of biochemical signals which initiate cell replication. They are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, *Advances in Cancer Research*, 1993, 60, 43-73) based on families of growth factors which bind to different receptor tyrosine kinases. The classification includes Class I receptor tyrosine kinases comprising the EGF family of receptor tyrosine kinases such as the EGF, TGFα, NEU, erbB, Xmrk, HER and let23 receptors, Class II receptor tyrosine kinases comprising the insulin family of receptor tyrosine kinases such as the insulin, IGFI and insulin-related receptor (IRR) receptors and Class III receptor tyrosine kinases comprising the platelet-derived growth factor (PDGF) family of receptor tyrosine kinases such as the PDGFα, PDGFβb and colony-stimulating factor 1 (CSF1) receptors.

It is known that Class I kinases such as the EGF family of receptor tyrosine kinases are frequently present in common human epithelial cancers such as breast cancer (Sainsbury et al., *Brit. J. Cancer*, 1988, 58, 458; Guerin et al., *Oncogene Res.*, 1988, 3, 21 and Klijn et al., *Breast Cancer Res. Treat.*, 1994, 29, 73), non-small cell lung cancers (NSCLCs) including adenocarcinomas (Cerny et al., *Brit. J. Cancer*, 1986, 54, 265; Reubi et al., *Int. J. Cancer*, 1990, 45, 269; and Rusch et al., *Cancer Research*, 1993, 53, 2379) and squamous cell cancer of the lung (Hendler et al., *Cancer Cells*, 1989, 7, 347), bladder cancer (Neal et al., *Lancet*, 1985, 366), oesophageal cancer (Mukaida et al., *Cancer*, 1991, 68, 142), gastrointestinal cancer such as colon, rectal or stomach cancer (Bolen et al., *Oncogene Res.*, 1987, 1, 149), cancer of the prostate (Visakorpi et al., *Histochem. J.*, 1992, 24, 481), leukaemia (Konaka et al., *Cell*, 1984, 37, 1035) and ovarian, bronchial or pancreatic cancer (EP-A-0400586). As further human tumour tissues are tested for the EGF family of receptor tyrosine kinases it is expected that their widespread prevalence will be established in further cancers such as thyroid and uterine cancer. It has been shown more recently (W J Gullick, *Brit. Med. Bull.*, 1991, 47, 87) that EGF receptors which possess tyrosine kinase activity are overexpressed in many human cancers such as brain, lung squamous cell, bladder, gastric, breast, head and neck, oesophageal, gynaecological and thyroid tumours.

Accordingly it has been recognised that an inhibitor of receptor tyrosine kinases should be of value as a selective inhibitor of the growth of epithelial cancer cells (Yaish et al. *Science*, 1988, 242, 933).

It is known from EP-A-0566226 and International Patent Applications WO-A-96/33980 and WO-A-97/30034 that certain quinazoline derivatives which possess an anilino substituent at the 4-position possess EGFR tyrosine kinase inhibitory activity and are inhibitors of the proliferation of cancer tissue.

It is further known from International Patent Applications WO-A-96/30347 and WO-A-97/38983 that certain structurally-related quinazoline derivatives possessing an anilino substituent at the 4-position also possess EGFR tyrosine kinase inhibitory activity.

Subsequently many other 4-anilinoquinazoline derivatives and structurally-related compounds thereof have been shown to possess EGFR tyrosine kinase inhibitory activity. Any such compound possessing that activity and adequate bioavailability is suitable for use in the present invention.

Particular compounds which have been stated to possess potent EGFR tyrosine kinase inhibitory activity include: —

N-(3-chloro-4-fluorophenyl)-7-methoxy-6-(3-morpholino propoxy)quinazolin-4-amine (identified hereinafter by the code number ZD1839);

N-(3-ethynylphenyl)-6,7-bis(2-methoxyethoxy)quinazolin-4-amine (identified hereinafter by the code number CP358774);

6-acrylamido-N-(3-chloro-4-fluorophenyl)-7-(3-morpholinopropoxy) quinazolin-4-amine (identified hereinafter by the code number PD0183805) disclosed, for example, in *J. Med. Chem.*, 1999, 42, 1803-1815; and pyrrolopyrimidine (identified hereinafter by the code number PKI 166 (CGP75166)).

All of the above relates to treatment of full cancer cells. Thus, it was believed that such EGFR tyrosine kinase inhibitors operate to inhibit the downstream signalling for the EGFR in ER– cancer cells and thereby inhibit proliferation of such cells.

As to normal cells, it is known that EGF may have a mitogenic effect in a variety of non-transformed epithelial cells grown in culture (Carpenter et al., *Annual Reviews in Biochemistry*, 1979, 48, 193) including cells from mouse mammary glands but that EGF can also have a growth inhibitory effect in certain cell lines and in naturally proliferating mammary tissue in mice (Coleman et al., *Developmental Biology*, 1990, 137, 425).

We have now found that EGFR tyrosine kinase inhibitors have effects not only on the growth of transformed epithelial cancer cells but also on the constitutive growth of normal epithelial cells. In, for example, normal human mammary epithelial tissue in the woman, oestrogen stimulates normal growth and induces the expression of the progesterone receptor. This allows, the hormonal effects of a second sex steroid to be mediated in the breast epithelium. Constitutive growth of, for example, mammary epithelial cells comprises the non-oestrogen dependent baseline turnover of cells which decreases with the age of the woman and after the menopause.

Thus using a xenograft model involving the implantation and growth of human normal breast tissue and in situ breast cancer in athymic BALB/c nu/nu mice (Holland et al., *J. National Cancer Institute*, (1997), 89, 1059 and Gandhi et al, *Cancer Research*, (2000), 60, 4284-4288), we have now found that EGFR tyrosine kinase inhibitors have effects on the constitutive and oestrogen-stimulated proliferation of premenopausal benign and pre-malignant [Ductal Carcinoma In Situ (DCIS)] breast epithelium. The inhibitory effect on constitutive and oestrogen-stimulated growth provides a method for inhibition of the transformation of normal cells into cancerous cells i.e. the basis for the chemopreventative treatment of women, particularly those at higher risk of developing malignant breast cancer.

An EGFR tyrosine kinase inhibitor may therefore be used to reduce, preferably to inhibit, the transformation of epithelial cells, in particular mammary epithelial cells, from a normal to a malignant state.

Given that EGF is known to be able to have a growth inhibiting effect on certain cell lines and naturally proliferating mammary tissue in mice, presumably via its growth receptor, it is surprising that a compound which actually blocks such growth reception (an EFGR inhibitor) should also reduce proliferation.

Thus, unlike conventional antioestrogens such as Tamoxifen, which effectively operate to block the effect of oestrogen upon the oestrogen receptor and lower EGF/TGFα production by the cell, and contrary to the previously mentioned mechanism of operation of EGFR inhibitors upon ER− cancer cells (again associated with EGFR blockage), it is believed that the EGFR inhibitors, when administered to in vivo benign mammary epithelium or to in vivo non-invasive mammary cancer (whether ER+ or ER−), are operative by blocking directly the cell proliferating role of the tyrosine kinase. Thus, by directly blocking the EGFR tyrosine kinase, the nature of the hormone sensitivity of the cells becomes irrelevant; i.e., the drugs operate by a non-hormonal mechanism.

In more detail, referring firstly to cell growth, in the breast, most growth cells are EGFR+ and ER−. In the absence of an EGFR inhibitor, oestrogen stimulates (only) ER+ cells, which secrete EGF production, which in turn acts on the ER− cells in a paracrine manner to induce proliferation. EGFR TK inhibitors of the invention bind to EGFR directly on ER− cells to inhibit such proliferation.

On the other hand, cell death (apoptosis) is prevented by survival signals from both tissue matrix and growth factors. Insulin like growth factor (IGFI) signals through the IGFI Receptor to prevent cell death in the breast.

Recent work by Roudabush et al (*J. Biol. Chem.*, (2000), 275, 22583-22589) has demonstrated that the IGFR stimulation induced by IGFRs leads to secretion of an EGF family member outside the cell which then acts on the cell's own, and neighbouring cells', EGFR. Blockade of the EGFR in the breast by EGFR TK inhibitors in the invention therefore leads to cell death (apoptosis) in vitro and in vivo in breast epithelium.

Surprisingly, the EGFR TKI can act directly, not only on the EGFR expressed on the ER− cells but independently upon ER+ cells.

R B Clarke et al, in Cancer Research (1997 57 4987-4991) have shown that normal ER+/EGFR− epithelial breast cells do not proliferate whilst neighbouring ER−/EGFR+ cells do, indicating that proliferation occurs by two mechanisms, namely oestrogen stimulation of (1) ER+ cells and
(2) EGF and related ligands secreted by ER+ cells so as paracrinely to stimulate neighbouring EGFR+/ER− cells.

By inhibiting TK with EGFR TKI, neighbouring ER−/EGFR+ cells are prevented from proliferating.

In addition, our data demonstrates that the EGFR TKI also prevents expression of the oestrogen induced progesterone receptor in ER+ cells and reduces ER+ cell turnover.

Thus, oestrogen induces steroid hormone receptor and protein synthesis in normal ER+ cells to enable proliferation and growth and hormone responsiveness of a cell and to secrete growth stimulating factors (e.g. EGF) which act on neighbouring ER− breast epithelial cells.

Additionally, EGFR TK inhibitors prevent the induction of the progesterone receptor by oestrogen in ER+ cells, thus reducing hormonal sensitivity and stimulation of breast epithelium and preventing transformation of normal to cancer tissue.

The progesterone receptor labelling index (PRLI), which falls in normal breast tissue unexposed to pre-menopausal levels of oestrogen to around 5%, is increased on exposure to oestrogen to 15% (I J Laidlaw et al, Endocrinology (1994), 136, 164-171). The use of ZD 1839 to antagonise oestrogen stimulation abrogates this rise leading to a PRLI of 10%.

In addition, an EGFR tyrosine kinase inhibitor may be used on epithelial tissue, in particular mammary epithelial tissue, which has developed to a non-invasive intermediate stage between normal epithelium, in particular normal breast epithelium, and malignant invasive epithelium, in particular malignant invasive breast epithelium, either to prevent proliferation of such cells or to cause the epithelial tissue in such cells substantially to revert back to a normal state.

Examples of such intermediate stage cells are those associated with atypical ductal hyperplasia, lobular neoplasia and non-invasive in-situ cancer cells present within the duct and/or lumen of a breast. Such cells may be present in patients at high risk of breast cancer.

According to a first aspect of the present invention there is provided the use of an EGFR tyrosine kinase inhibitor in the manufacture of a medicament for use in reducing, preferably inhibiting, the transformation of epithelial cells, in particular mammary epithelial cells, from a normal to a malignant state in an invasive breast cancer free human, especially a woman.

According to a second aspect of the present invention there is provided the use of an EGFR tyrosine kinase inhibitor in the manufacture of a medicament for use in reducing, preferably inhibiting, the transformation of epithelial cells, in particular mammary epithelial cells, from an intermediate state, as defined above, to a malignant state in an invasive breast cancer free human, especially a woman.

The invention, according to each of these first and second aspects, is particularly applicable to patients at high risk of breast cancer, so-called "high risk" patients. It is known to classify high risk patients as being those having a score of at least 1.5 on the so-called Gail Risk Model, a computer generated programme acceptable for assessment of the risk of breast cancer (see M. H. Gail et al, J. Natl. Cancer Inst., (1989), 81, 1879-1886). Factors which increase the risk of developing breast cancer include the presence of intermediate cells associated with atypical hyperplasia (including a history of this as indeed of breast cancer in a first relative), lobular neoplasia, non-invasive in-situ cancer or the presence of a mutant BRCAI gene (see D. L. Page et al, BMJ, (1994), 309, 61-64).

Thus, the invention is especially applicable to the treatment of intermediate cells.

In a preferred version of the above mentioned first aspect of the invention there is provided the use of an EGFR tyrosine kinase inhibitor selected from ZD1839, CP358774, PD0183805 and PKI 166 in the manufacture of a medicament for use in inhibiting the transformation of mammary epithelial cells from a normal to a malignant state in a human, especially a woman.

In a more preferred version of this aspect of the invention there is provided the use of the EGFR tyrosine kinase inhibitor ZD1839 in the manufacture of a medicament for use in inhibiting the transformation of mammary epithelial cells from a normal to a malignant state in a human, especially a woman.

In a preferred version of the above mentioned second aspect of the invention there is provided the use of an EGFR tyrosine kinase inhibitor selected from ZD1839, CP358774, PD0183805 and PKI 166 in the manufacture of a medicament for use in inhibiting the transformation of mammary epithelial cells from an intermediate to a malignant state in a human, especially a woman.

In a more preferred version of this aspect of the invention there is provided the use of the EGFR tyrosine kinase inhibitor ZD1839 in the manufacture of a medicament for use in inhibiting the transformation of mammary epithelial cells from an intermediate to a malignant state in a human, especially a woman.

According to a third aspect of the present invention there is provided a method for reducing, preferably inhibiting, the transformation of epithelial cells, in particular mammary epithelial cells, from a normal to a malignant state in an invasive breast cancer free human, especially a woman, which comprises the administration of an effective amount of an EGFR tyrosine kinase inhibitor.

In a preferred version of this third aspect of the invention there is provided a method for inhibiting the transformation of mammary epithelial cells from a normal to a malignant state in a human, especially a woman, which comprises the administration of an effective amount of an EGFR tyrosine kinase inhibitor selected from ZD1839, CP358774, PD0183805 and PKI 166.

In a more preferred version of this aspect of the invention there is provided a method for inhibiting the transformation of mammary epithelial cells from a normal to a malignant state in a human, especially a woman, which comprises the administration of an effective amount of the EGFR tyrosine kinase inhibitor ZD1839.

According to a fourth aspect of the present invention there is provided a method for reducing, preferably inhibiting, the transformation of epithelial cells, in particular mammary epithelial cells, from an intermediate to a malignant state in an invasive breast cancer free human, especially a woman, which comprises the administration of an effective amount of an EGFR tyrosine kinase inhibitor.

In a preferred version of this fourth aspect of the invention there is provided a method for inhibiting the transformation of mammary epithelial cells from an intermediate to a malignant state in a human, especially a woman which comprises the administration of an effective amount of an EGFR tyrosine kinase inhibitor selected from ZD1839, CP358774, PD0183805 and PKI 166.

In a more preferred version of this aspect of the invention there is provided a method for inhibiting the transformation of mammary epithelial cells from an intermediate to a malignant state in a human, especially a woman, which comprises the administration of an effective amount of the EGFR tyrosine kinase inhibitor ZD1839.

As in the case of the first and second aspects of the invention, these third and fourth aspects of the invention are particularly applicable to high risk patients and to treatment of intermediate cells, as hereinbefore defined.

According to a fifth aspect of the present invention there is provided the use of an EGFR tyrosine kinase inhibitor in the manufacture of a medicament for use in causing substantial reversion of epithelial tissue, in particular mammary epithelial tissue, back to a normal state from the intermediate state, as previously defined, between normal epithelium, in particular normal breast epithelium, and malignant invasive epithelium, in particular malignant invasive breast epithelium.

In a preferred version of this fifth aspect of the invention there is provided the use of an EGFR tyrosine kinase inhibitor selected from ZD1839, CP358774, PD0183805 and PKI 166 in the manufacture of a medicament for use in causing substantial reversion of mammary epithelial tissue back to a normal state from an intermediate state between normal breast epithelium and malignant invasive breast epithelium.

In a more preferred version of this fifth aspect of the invention there is provided the use of the EGFR tyrosine kinase inhibitor ZD1839 in the manufacture of a medicament for use in causing substantial reversion of mammary epithelial tissue back to a normal state from an intermediate state between normal breast epithelium and malignant invasive breast epithelium.

According to a sixth aspect of the present invention there is provided a method for causing substantial reversion of epithelial tissue, in particular mammary epithelial tissue, back to a normal state from an intermediate state between normal epithelium, in particular normal breast epithelium, and malignant invasive epithelium, in particular malignant invasive breast epithelium which comprises the administration to an invasive breast cancer free human, especially a woman, of an effective amount of an EGFR tyrosine kinase inhibitor.

In a preferred version of this sixth aspect of the invention there is provided a method for causing substantial reversion of mammary epithelial tissue back to a normal state from an intermediate state between normal breast epithelium and malignant invasive breast epithelium which comprises the administration to a human, especially a woman, of an effective amount of an EGFR tyrosine kinase inhibitor selected from ZD1839, CP358774, PD0183805 and PKI 166.

In a more preferred version of this sixth aspect of the invention there is provided a method for causing substantial reversion of mammary epithelial tissue back to a normal state from an intermediate state between normal breast epithelium and malignant invasive breast epithelium which comprises the administration to a human, especially a woman, of an effective amount of the EGFR tyrosine kinase inhibitor ZD1839.

In use, the EGFR tyrosine kinase inhibitor may be administered alone or in a composition containing a pharmaceutically acceptable excipient. Preferably, it is administered in tablet form.

It will generally be administered so that an effective, non-toxic dose is given. The size of the dose will naturally vary according to the particular EGFR tyrosine kinase inhibitor which is chosen and the route of administration to the patient. In general conventional doses of each EGFR tyrosine kinase inhibitor can be employed. In particular, for the EGFR tyrosine kinase inhibitors CP358774, PD0183805 and PKI 166, conventional doses according to publications concerning these compounds can be employed. More particularly, for the EGFR tyrosine kinase inhibitor ZD1839, a daily dose is administered in the range, for example, from about 10 mg to 5 g, preferably from about 10 mg to 1000 mg, more preferably from about 10 mg to 500 mg (i.e. about 0.2 mg/kg to 100 mg/kg body weight, preferably from about 0.2 mg/kg to 20 mg/kg body weight, more preferably from about 0.2 mg/kg to 10 mg/kg body weight), given if required in divided doses.

The inhibition of cellular transformation defined hereinbefore may be applied as a sole therapy or may involve, in addition to an EGFR tyrosine kinase inhibitor such as ZD1839, one or more other substances and/or treatments. Such conjoint treatment may be achieved by way of the simultaneous, sequential, separate or intermittent administration of the individual components of the treatment. For example, in women at above average risk of developing breast cancer, when the EGFR tyrosine kinase inhibitor is used to inhibit the transformation of mammary tissue into breast cancer, it may be normal practice to use a combination of different forms of treatment. The other component of such conjoint treatment may include an antioestrogen such as tamoxifen, fulvestrant (ICI 182,780: faslodex) or raloxifene. It may then be beneficial to employ sequential therapy with, for example, a first treatment period of about 1 to 6 months during which a conventional dose of an EGFR tyrosine kinase inhibitor such as ZD1839 is administered followed by a second treatment period of about 1 to 6 months during which a conventional dose of an antioestrogen such as tamoxifen, fulvestrant or raloxifene is administered. Thereby a period is allowed whereby some constitutive growth of mammary tissue is permitted in order to minimise the extent of tissue atrophy.

Alternatively the combination therapy may include the continuous administration of an antioestrogen such as tamoxifen, fulvestrant or raloxifene and the intermittent administration of an EGFR tyrosine kinase inhibitor such as ZD1839. The intermittent therapy of the EGFR tyrosine kinase inhibitor may involve, for example, a two-monthly cycle of treatment comprising a first portion involving the dosing of the EGFR tyrosine kinase inhibitor such as ZD1839 for a period of about one month followed by a second portion involving an EGFR tyrosine kinase drug-free period of about one month. Thereafter further two-monthly cycles of such treatment may be given.

Embodiments of the invention will now be described in more detail with reference to the following Examples and accompanying drawings in which:

EXAMPLE 1

Figure 1:
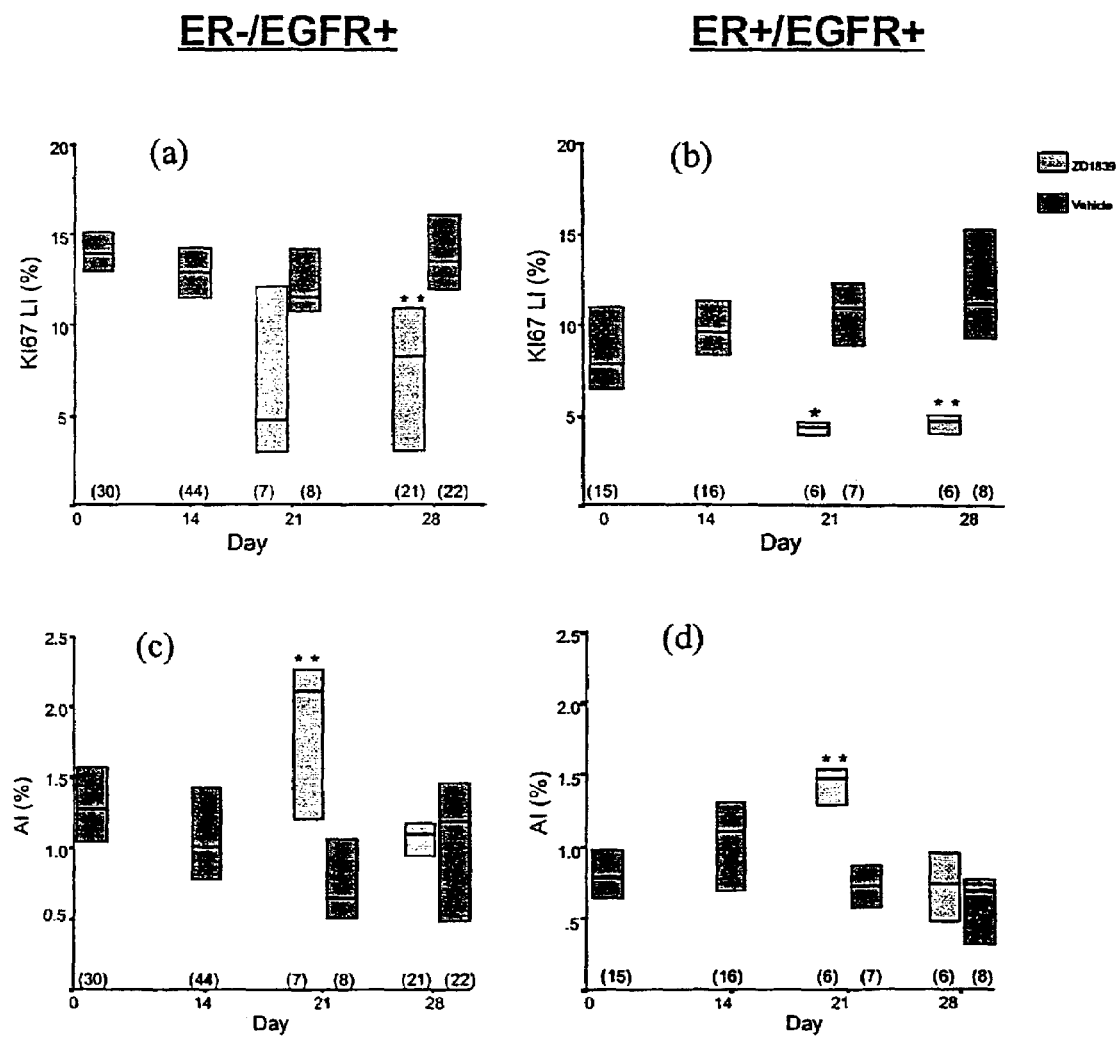
FIG. 1 illustrates, for Example 2, proliferation (Ki67 LI) and apoptosis (AI) in ER–/EGFR+ and ER+/EGFR– DCIS epithelium.

The effect of the EGFR tyrosine kinase inhibitors of the present invention was determined using a xenograft model involving the implantation and growth of human normal breast tissue and in situ breast cancer in female athymic BALB/c nu/nu mice (Holland et al., *J. National Cancer Institute*, 1997, 89, 1059 and Gandhi et al, *Cancer Research*, (2000), 60, 4284-4268). Normal breast tissue and ductal carcinoma in situ (DCIS) tissue from women undergoing therapeutic surgery was implanted as xenografts into female mice. After 14 days, daily dosing of ZD1839 at 10 to 200 mg/kg was commenced for a 14 day period. Xenograft tissue was excised at days 0, 14, 21 and 28. Pellets of 17β-estradiol (2 mg) were implanted subcutaneously in a second set of experiments (using normal breast xenografts) on day 14 in both control and treatment mice and conventional Ki67 immunostaining was used to assess epithelial proliferation (Ki67 is a monoclonal antibody to a marker in a cell).

The following results were obtained: —

| Ki67 index Normal breast | Day 0 Control | Day 21 Control | Day 21 ZD1839 Group | Day 28 Control | Day 28 ZD1839 Group |
|---|---|---|---|---|---|
| Median | 7.6 | 3.3 | 0.7 | 6.1 | 1.8 |

| KiG7 index DCIS tissue | Day 0 Control | Day 21 Control | Day 21 ZD1839 Group | Day 28 Control | Day 28 ZD1839 Group |
|---|---|---|---|---|---|
| Median | 19.9 | 10.6 | 7.2 | 23 | 3.2 |

| Ki67 index Oestrogen-stimulated Normal breast | Day 0 Control | Day 21 Control | Day 21 ZD1839 Group | Day 28 Control | Day 28 ZD1839 Group |
|---|---|---|---|---|---|
| Median | 10.4 | 15.7 | 1.5 | 14.8 | 1.2 |

EXAMPLE 2

Summary of Procedure

Breast tissue from 16 women undergoing surgery for DCIS were implanted into 16-20 immunosupressed mice per experiment (8 xenografts/mouse). Treatment commenced 2 weeks post implant and consisted of daily gavage with ZD1839 at 10-200 mg/Kg for 14-28 days; appropriate controls were present. Xenografts were removed on Days 14, 21, 28 and 42 and then assessed for proliferation (LI) by Ki67 immunostaining, and apoptosis (AI) by morphology.

Materials and Methods

Patients

Participants in this study were women who either attended the Nightingale Breast Screening Assessment Centre or the Symptomatic Breast Clinic at the University Hospital of South Manchester, U.K. during the period November 1998 to January 2000. Women were included in the study if they had mammograms showing widespread microcalcification indicative of DCIS and either cytopathological or histopathological confirmation of the diagnosis (n=16). All tissue samples were obtained at therapeutic excision of DCIS. Approval to remove tissue from pathologic samples in this study was granted by the South Manchester Medical Research Ethics Committee.

Animals

Intact, adult, female, 8-10 week-old, athymic nude mice (BALB/c nu/nu) were obtained from the breeding colony at the Paterson Institute for Cancer Research. They were housed under conventional conditions with a 12-hour cycle of light and dark (lights off from 7 PM to 7 AM) in filter top cages. They were supplied ad libitum with irradiated feed and filtered water and irradiated bedding during breeding. Normal food, water, and bedding were used during the experiments.

All care of the animals and surgical procedures were performed in accordance with Home Office Regulations and the UK Scientific Procedures (1986) Act. Halothane inhalational anaesthesia (24% halothane on oxygen; Halovet Vapouriser, International Market Supplies, Congleton, U.K.) was used for all procedures.

Treatment of Tissue Samples

For preparation of tissue specimens for grafting to mice, 1-2 cm$^3$ pieces of breast tissue, containing microcalcifications, were taken at the time of surgery from the main specimen. The fresh tissue was stripped of excess fat and immediately divided under sterile conditions into three or four smaller portions and placed in Dulbecco's Modified Eagle Medium (DMEM), with 4.5 g/L glucose and without sodium pyruvate (Gibco Life Technology, Paisley, Scotland, UK) at room temperature until implantation into the mice. In the laboratory, the tissue was placed into fresh DMEM in a sterile Petri dish, and the tissue was carefully dissected into 2-mm× 2-mm×1-mm samples with a scalpel blade. Depending on the volume of tissue available, between 5 and 20 pieces were randomly selected from the Petri dish and not implanted into the mice but instead were used for histology. Half of these nonimplanted (day 0) grafts were immediately fixed in buffered formalin (4% formaldehyde) for 24 hours, and the other half in Carnoy's fixative for 1 hour, and then all were stored in 70% alcohol. Following at least 24 hours, the fixed tissue samples were placed individually in tissue cassettes (Tissue Tek III; Bayer Diagnostics Ltd., Basingstoke, UK.) and stored in 70% alcohol until paraffin embedding. These samples representing the DCIS excised from the each patient, were labelled as the "Day O" specimens, and were reserved for histological review, immunostaining, and apoptotic cell counts. The remaining xenografts were implanted into nude mice.

Implantation of Xenografts into Nude Mice

As in Example 1, each patient's sample was divided between 10 and 32 mice (depending on the volume of tissue and number of mice available; median number, sixteen). Transplantation of xenografts onto the mice was completed within 90 minutes of removal of tissue from the patient. Two small midline skin incisions were made across the dorsal skin through which 8 tissue pieces were symmetrically placed (4 on each side). Retrieval of these xenografts at the appropriate time points required reanaesthetizing the mice and excising each graft using sharp dissection. The grafts were then processed for histology as described above for the Day 0 specimens. For the 100-200 mg/kg ZD1839 experiments, grafts were removed on Days 14, 21 and 28; at the lower doses (10-75 mg/kg), grafts were retrieved on Days 14, 28, and 42. Two xenografts were removed at each interim time point and 4 xenografts at each end time points from each mouse.

Treatment

The mice were gavaged for 14-28 days with either ZD1839 (10-200 mg/kg) or vehicle commencing on Day 14 after removal of the first 2 xenografts. ZD1839 (4-(3-chloro-4fluorophenylamine)-7-methoxy-6(3-(4morpholinyl)quinazoline), an orally active, selective EGFR-TKI was a kind gift of AstraZeneca Pharmaceuticals. The vehicle (control) was 0.5% polysorbate.

Histological Evaluation of Xenografts

All Day 0 specimens and each xenograft were embedded into paraffin blocks. H&E stained, 3-μm sections from each block were examined by a single experienced breast pathologist for the presence of DCIS; those containing DCIS were assessed for apoptosis and Ki67 antigen immunogenicity (as a marker of epithelial proliferation) as previously described.

Nuclear grade and the presence or absence of comedonecrosis were also ascertained on all Day 0 specimens containing DCIS. In addition, Day 0 specimens were evaluated immunohistochemically for ER, c-erbB-2, EGFR status.

Assessment of Apoptotic Cell Death

H&E-stained sections of DCIS samples were examined using light microscopy for morphological evidence of apoptosis. The criteria used to identify apoptotic cells are well recognised, and include condensation of chromatin initially at the margins of the nucleus; condensation of the cytoplasm (chromophilia); detachment from the surrounding cells, indicated by the appearance of a characteristic white halo around the dying cell; and cytoplasmic budding to form membrane-bound fragments (apoptotic bodies). To acquire the AI, at least 1000 cells were counted at ×400 magnification using a Zeiss microscope, and the number of cells displaying apoptotic morphology were expressed as a percentage of the total number counted.

Immunohistochemical Determination of ER and Ki67 Nuclear Antigen

ER and Ki67 immunohistochemical methodology were employed. These have been previously described (Gandhi et al, *Br. J. Cancer*, (1998), 78, 785-794).

Both ER and Ki67 staining were predominantly nuclear with minimal cytoplasmic uptake. The intensity of staining was variable, but this was not assessed separately, and the cells were judged as positive or negative. The Ki67 the Labelling Index (LI) was calculated from counting a minimum of 1000 epithelial cells and the number of positively stained nuclei were expressed as a percentage of the total number counted. The ER status was determined also counting at 1000 cells, and lesions were considered ER+ if >5% of cells were positively stained for ER Immunohistochemical Determination of c-erbB-2, EGFR and pErk1/Erk2

Paraffin wax sections (3 μm thick) of tissue from each specimen were cut, mounted on APES (3-aminopropylethoxysilane) coated slides, dewaxed and hydrated before immunohistochemical staining for the c-erbB-2, EGFR and phosphorylated (p) Erk1/Erk2. Antigen retrieval was achieved by a microwave method (650 W) for 30 minutes (min). Endogenous peroxidase activity was blocked by incubation in hydrogen peroxide [1.5% (v/v) for EGFR and c-erbB-2, 3% (v/v) for pErk1/Erk2] in phosphate-buffered saline (PBS) for 15 min. For the c-erbB-2 and EGFR antigen, the slides were rinsed in TBS prior to using 10% normal rabbit serum to block non-specific binding and then incubated with the primary antibody at a dilution of 1:20 for EGFR (mouse monoclonal anti-human, NCL-EGFR; Novocastra labs, Newcastle upon Tyne, UK) and at a dilution of 1:40 for c-erbB-2 (mouse monoclonal, MAB4022, Chemicon, Harrow, UK), for 1 hour at room temperature. A biotinylated rabbit anti-mouse immunoglobulin (E413, Dako, High Wycombe, UK) was applied as the secondary antibody (1:350 dilution, incubated for 30 min), and following this a 30 min incubation at RT with the standard three layered streptavidin-avidin-biotin horseradish (K0377, Dako) for c-erbB-2 and EGFR. For pErk1/Erk2 antigen detection, the sections were blocked with 20% normal human serum for 15 min prior to application of the polyclonal rabbit antihuman pMEK, pErk1/Erk2, pElk1 primary antibodies at a dilution of 1:20 (9101 L, New England Biolabs, UK). Biogenex Multil Link at a dilution of 1:100 (Euro/DPC, Llanberis, UK) was applied as the secondary antibody for 1 hr. An avidin/biotin complex immunohistochemical kit procedure (Biogenex Concentrated Label, Euro/DPC) was employed.

The chromogen diaminobenzidine (Sigma, Poole, UK) was applied for 5 min and then haematoxylin as counterstain for 5 min.

Negative (generic mouse IgG, X0931, Dako) and positive controls (sections of A431 cells for EGFR, and of DCIS tissue previously shown to be strongly positive for c-erbB-2 and pErk1/Erk2) were used.

Staining for c-erbB-2 and EGFR were predominantly membranous but there was also cytoplasmic and nuclear uptake. These were scored positive (scale 14) or negative in relation to the positive and negative control slides. Staining for pErk1/Erk2 was nuclear and cytoplasmic and scored according intensity of staining in the nuclear and cytoplasmic components as previously described (Gee et al, *Int. J. Cancer*, (1995), 64, 269-273).

All histological assessments were performed by investigators blinded to the treatment group. Reproducibility of counting was assessed by the same investigator re-scoring 10 slides stained with the Ki67 antibody and 10 H&E slides for apoptosis several months after initial estimation. The two sets of results thus obtained were well correlated by regression analysis ($r=0.95$, $P<0.001$)

Epithelial Proliferation in Normal Mouse Intestine

Removal, processing of intestinal tissue for Ki67 assessment, and scoring methodology has been previously described (Potten and Grant, *Br. J. Cancer*, (1998), 78, 993-1003).

Statistical Methods

Statistical analysis was performed using SPSS software (SPSS, Chicago, Ill., USA) by the CRC Department of Computing and Biomathematics at the Paterson Institute for Cancer Research. For each case showing normal breast epithelium or DCIS, a comparison was made between samples retrieved from ZD1839 treated and control mice at each assessment time point. The tissue samples obtained at each assessment time in the two study groups were considered to be statistically independent and were compared using the Mann Whitney U test. All significance tests were two-sided, using the conventional 5% significance level. Data from the separate ZD1839 doses were collapsed after initial analysis demonstrated effect at all doses. Pearson's correlation coefficient was used to examine the degree of correlation between metric variables. Statistical analysis of proliferation in intestinal epithelium was by comparing medians at each epithelial cell position in the crypts.

Results

The median age of women who were undergoing surgery was n=range (menopausal status).

Xenograft Implant and Retrieval

DCIS

Of the 16 breast tissue specimens found to contain DCIS at surgery, 13 (81.3%) produced Day 0 specimens which contained DCIS, of which 11 immunohistochemically expressed EGFR+ with a median score of 2 (range 1-3), and 2 were EGFR-. Of these 11 EGFR+ cases, 7 were ER-/c-erbB-2 positive (all high nuclear grade), and 3 ER+/c-erbB-2 positive (1 high grade, 2 intermediate grade), and 1 ER+/c-erbB-2 negative (low grade). The 13 breast tissue specimens gave rise to a total of 273 Day 0 samples of which 44 (16.1%) contained foci of DCIS. A total of 1904 xenografts were implanted, of which 1858 (97.5%) were successfully retrieved. Of the 1858 xenografts retrieved, 329 (17.7%) contained DCIS. The median retrieval of DCIS per experiment was 71% of that expected (range 14-91.3%). DCIS was retrieved at Days 14, 21, 28, and 42 xenografts in all of the 13 experiments.

Normal Breast

Histologically normal breast tissue was found in all 16 specimens removed from surgery for DCIS. The majority (97.6%) of the xenografts implanted were retrieved, of which 22.4% contained normal breast Normal breast was retrieved from all the time points in 100% of all of the experiments. All 16 cases were ER+ and EGFR+ with a median score of 1 (range 1-2), and 2 were also weakly c-erbB-2 positive.

Normal Breast (Table 1)

Table 1 shows EGFR+ proliferation (LI) and apoptosis (AI) in ZD1839 (10-200 mg/kg [collapsed data]) versus vehicle-treated (a) normal breast and (b) DCIS epithelium at the different time points. Numbers in parentheses represent the interquartile ranges $p<0.01$, *$p<0.001$ versus control.

Normal breast xenografts had a decrease in median LI from Days 0 to 14 (4.9 [IQR: 4.0-5.7] versus 3.8 [IQR: 2.7-5.1], $p<0.05$) which then remained unchanged for the other time points (Days 21, 28, and 42). Median LI decreased in the ZD1839 treated group compared to controls at Day 21 (2.3 [IQR: 1.0-3.8] versus 4.1 [IQR: 2.8-5.2]), Day 28 (2.2 [IQR: 1.7-3.3] versus 4.1 [IQR: 2.4-5.4]), and Day 42 (1.7 [IQR: 1.1-2.6] versus 2.8 [IQR: 2.3-5.1]) (all $p<0.01$).

The AI findings were similar findings to the DCIS treated xenografts above. No reduction in median AI was observed from Day 0 to 14 (0.20 [IQR: 0.17-0.29] versus 0.18 [IQR: 0.10-0.21], $p=0.90$). At Day 21, there was an increase in median AI in ZD1839 treated xenografts compared to controls (0.36 [IQR: 0.23-0.53] versus 0.18 [IQR: 0.10 to 0.25, $p<0.001$). After 14 days of treatment (Day 28), median AI equilibrated to control levels (ZD1839 0.19 [IQR: 0.10-0.28] versus Control 0.18 [IQR: 0.10-0.20], $p=0.35$).

TABLE 1

The effect of ZD1839 on proliferation and apoptosis on normal breast and DCIS epithelium

| Median | Day 0 | Day 14 | Day 21 | | Day 28 | |
| --- | --- | --- | --- | --- | --- | --- |
| | | | Control | ZD1839 | Control | ZD1839 |
| LI | | | | | | |
| Normal breast | 4.9 | 3.8 | 4.1 | 2.3** | 3.4 | 2.2** |
| | (4.0-5.7) | (2.7-5.1) | (2.8-5.3) | (1.0-3.8) | (2.4-5.4) | (1.7-3.3) |
| DCIS | 13.9 | 12.6 | 11.2 | 4.6** | 13.1 | 5.1** |
| | (11.9-15) | (9.1-14.1) | (9.7-12.9) | (3.2-7.2) | (11.8-15.8) | (3.2-10.6) |

TABLE 1-continued

The effect of ZD1839 on proliferation and apoptosis on normal breast and DCIS epithelium

| Median | Day 0 | Day 14 | Day 21 | | Day 28 | |
|---|---|---|---|---|---|---|
| | | | Control | ZD1839 | Control | ZD1839 |
| AI | | | | | | |
| Normal breast | 0.20 | 0.18 | 0.18 | 0.36** | 0.18 | 0.19 |
| | (0.18-0.29) | (0.10-0.21) | (0.10-0.25) | (0.23-0.53) | (0.10-0.20) | (0.10-0.28) |
| DCIS | 1.07 | 0.79 | 0.72 | 1.47** | 0.46 | 0.64 |
| | (0.89-1.21) | (0.53-1.19) | (0.55-0.91) | (1.25-2.18) | (0.34-0.85) | (0.38-1.15) |
| LI/AI | | | | | | |
| Normal breast | 23.9 | 25.7 | 15.9 | 3.9*** | 33.8 | 8.5*** |
| | (18.3-43.3) | (13.4-33.3) | (8.0-26.3) | (1.6-5.2) | (21.4-70.6) | (5.8-17.4) |
| DCIS | 12.1 | 12.1 | 17.7 | 2.7*** | 29.7 | 4.4*** |
| | (8.4-15.8) | (8.2-19.9) | (12.7-22.0) | (2.2-3.6) | (13.1-40.2) | (2.7-6.9) |

EGFR+ DCIS (FIG. 1)

FIG. 1 shows changes in LI and AI induced by ZD1839 in ER−/EGFR+ (1a and 1c) and ER+/EGFR+ (1b and 1d) DCIS respectively. ZD1839 or vehicle was given from day 14 onwards. Values for days 0 and 14 are from untreated mice. An increase in AI and a decrease in LI was seen in the ZD1839 group following 7 and 14 days of treatment (*p<0.05, **p<0.01 versus control) in both ER−/EGFR+ and ER+/EGFR+ DCIS. Numbers in parentheses represent the number of observations seen for that particular time point and for that group. Median values are shown as thick horizontal lines, boxes represent interquartile range.

The median LI and AI in Day 0 specimens was higher in the 7 cases of ER−/EGFR+DCIS than the 4 cases of ER+/EGFR− DCIS (14.0 [IQR:13.0-15.3] versus 7.8 [IQR:6.5-11.2], and 1.3 [IQR: 1.0-1.6] versus 0.79 [IQR: 0.6-1.0] respectively, both p<0.05).

Median LI in ER−/EGFR+ DCIS decreased in the ZD1839-treated group compared to the vehicle-treated group by Day 21 (4.7 [IQR: 2.6-17.2] versus 11.6 [IQR: 10.7-15.1], p=0.19), Day 28 (8.3 [IQR: 2.7-10.9] versus 13.5 [IQR: 12.0-16.3], p<0.01), and Day 42 (11.4 [IQR: 10.8-11.8] versus 13.0 [IQR: 12.0-14.8], p<0.05) (FIG. 1a).

There was no change in median AI in ER−/EGFR+ DCIS from Day 0 to 14 (1.3 [IQR: 1.0-1.6] versus 1.0 [IQR: 0.8-1.44], p=0.14). Following 7 days of treatment (Day 21), there was a significant increase in median AI in the ZD1839-treated group compared to the vehicle-treated group (2.1 [IQR: 1.0-2.3] versus 0.7 [IQR: 0.5 to 1.1], p<0.01), although, after 14 days of treatment (Day 28), median AI returned to control levels (ZD1839 1.1 [IQR: 0.8-1.2] versus Control 1.2 [IQR 0.5-1.5], p=0.44) (FIG. 1b).

Similar changes in LI and AI in ER+/EGFR+DCIS (FIGS. 1b and 1d) were seen with a significant fall in LI at Day 14 (ZD1839 4.6 (IQR 3.9-5.2%) versus 11.2 Control (IQR 9.2-15.55) and a rise in apoptosis (ZD1839 1.5 (IQR 1.3-1.6) versus Control (IQR 0.6-0.9%).

Figure 2:
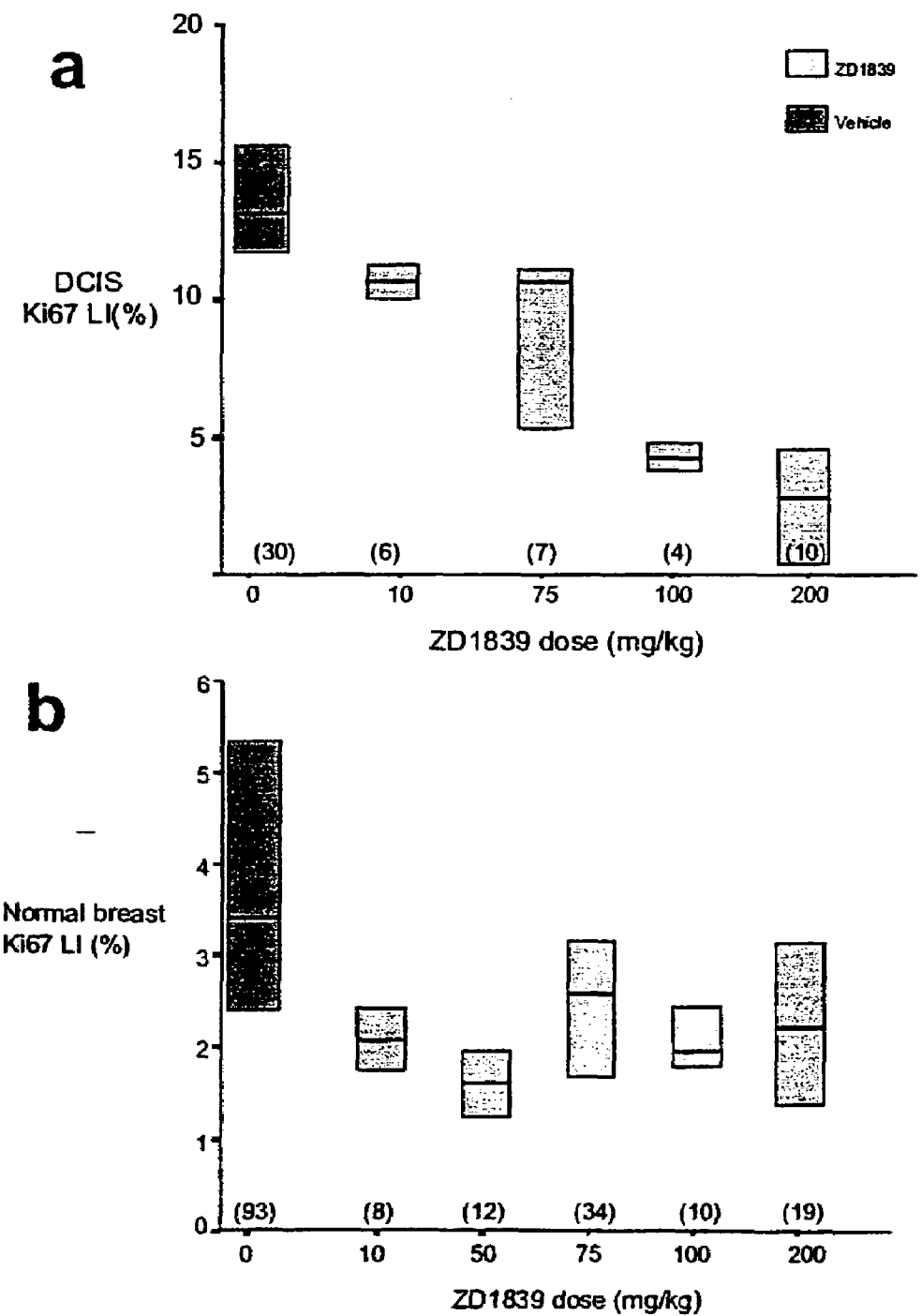
FIG. 2 illustrates, for Example 3, ZD18389 dose response in (a) DCIS and (b) normal breast.

K167 LI in EGFR+ (FIG. 2)

FIG. 2 shows epithelial proliferation rates (Ki67 LI) in EGFR+ (a) DCIS and (b) normal breast xenografts following 2 weeks (Day 28) of gavage with either different doses of ZD1839 (10-200 mg/kg) or vehicle control. Numbers in parentheses represent the number of observations seen for that particular time point and for that group. Median values are shown as thick horizontal lines, boxes represent interquartile range.

Increasing doses of ZD1839 were associated with increasing falls in epithelial proliferation in both ER−/EGFR+ and ER+/EGFR+ DCIS but not in normal breast (FIG. 2).

Correlation of Proliferation with Apoptosis

We have previously demonstrated a positive correlation of LI with AI in DCIS. LI displayed a positive correlation with AI in the normal breast and DCIS (r=0.10, p=0.02, and r=0.25, p<0.01 respectively) not treated by ZD1839 (i.e. Days 0, Day 14, and vehicle control cases).

Comparison of cell population using the median LI/AI ratio (as a ratio of cell turnover) revealed that ZD1839 treatment significantly inhibited cell turnover in both DCIS and normal breast at Day 28 (4.4 [2.7-6.9] versus 29.7 [13.1-40.2], and 8.5 [5.8-17.4] versus 33.8 [21.4-70.6] respectively, p<0.001.

Downregulation of pErk1/2 in EGFR TKI Treated DCIS and Normal Breast

To determine whether the MAP kinase signalling pathway is effected by EGFR tyrosine kinase inhibition, immunohistochemical detection of phosphorylated (p) ErK1/Erk2 was performed on Day 0 and Day 42 sections of DCIS and normal breast xenografts treated with ZD1839 or vehicle. Median Day 0 DCIS and normal breast nuclear HScore were 30 (IQR: 12-45) and 22 (IQR: 12-34). In DCIS, the nuclear HScore was decreased in the ZD1839 treated group compared to controls after 28 days treatment (8 [IQR: 5-18] versus 25 [IQR: 8-30], p<0.05). In normal breast there was a similar difference (7 [IQR: 3-17.5] versus 18 [IQR: 8-32], p<0.01).

The Nuclear HScore of pErK1/Erk2 correlated with the Ki67 LI in DCIS and in normal breast (both r=0.52, p=0.05).

Discussion

ER− DCIS overexpresses c-erbB-2 oncogene, and also is reported to express EGFR in 50% of cases. We found dual expression of both receptors on the same cell population in 10 out of 11 (90%) of ER− DCIS. ER− DCIS has a high proliferative rate, which in pre-treatment samples correlated with high expression of the MAP kinase signal transduction enzyme.

We therefore hypothesised that the formation of EGFR/c-erbB-2 heterodimers was responsible for the high proliferation rate and MAP kinase expression and we tested our theory by using an EGFR-TKI peptide, ZD1839. On ZD1839 treatment, a prolonged fall in epithelial proliferation and a decrease in activated MAP kinase expression was seen combined with an increase in apoptosis at an early stage confirming our hypothesis. EGFR is known to produce a mitogenic signal and correlates with proliferation and tumour doubling in invasive breast cancer, and inhibition of this pathway led to a fall in Ki67 labelling index in DCIS xenografts.

An increase in apoptosis was seen in both DCIS and normal breast epithelium after seven days of treatment. Although the Insulin Like Growth Factor-1 (IGF-1) is believed to be important in cell survival, recent work by Roudabush et al, *J. Biol. Chem.*, (2000), 275, 22583-22589, has indicated that IGF-1 receptor stimulation leads to secretion of heparin binding-EGF extracellularly and promotes transactivation in the EGF receptor. Thus, the EGFR may be more important to cell survival in the normal breast than has been previously recognised. Since epithelial proliferation correlates with apoptosis in the normal breast a reduction in proliferation would be expected to correlate with a reduction in apoptosis. After the initial increase in apoptosis after 7 days in the ZD1839 treated group the fall in labelling index (proliferation) led to a fall in apoptosis by 14 days. However the overall LI/AI ratio in the ZD1839 treated groups in both DCIS and normal breast was reduced indicating a lower overall cell turnover with EGFR-TK inhibition. Moreover, the overall fall in cell turnover indicates the potential chemopreventative effect of an EGFR TKI on normal breast.

ER– high grade DCIS is reported to be the most likely to relapse after wide local excision and at relapse at least 50% has become invasive high grade breast cancer with associated nodal or distant metastases. Prevention of relapse and progression to invasive cancer requires an agent which suppresses proliferation or increases apoptosis and the EGFR-TKI described fulfils this criteria.

A suppression of normal breast epithelial proliferation combined with an increase in apoptosis indicates the potential of EGFR-TK Inhibitors as chemoprevention agents in women at increased risk of breast cancer.

The EGFR MAP Kinase pathway is believed to be important in cell proliferation, survival and differentiation. The significant positive correlation of pErk1/Erk2 with Ki67 labelling index in DCIS and normal breast suggests that MAP kinase signalling is important in mediating cell proliferation in breast epithelium. A decrease in pErk1/Erk2 in the ZD1839 treated group correlated with a fall in proliferation and it is likely that the EGFR signals through this pathway and MAP kinase changes will predict drug response.

EXAMPLE 3

Using the method of Example 1, the procedural steps of which are described more fully in Example 2, the effect of ZD 1839 on proliferation (Ki67 LI) in oestrogen stimulated normal breast epithelium was measured. The results are shown in Table 2.

In the normal breast epithelium, on day 0, the date of implantation into a mouse, the Ki67 LI value was 4.1 and reduced to 2.6 on the 14th day. Control mice were then treated with oestrogen alone, while the test mice were treated with both oestrogen and ZD1839. The amount of oestrogen administered corresponded to a premenopausal level; i.e. 17-β-oestradiol pellet (2 mg) (see Holland et al, referred to in Example 1). After 21 days, the Ki67 LI value for the control mice was as high as 6.5, whereas for the test mice the value was considerably reduced to a value of 1.4. After 28 days, the Ki67 LI value for the control mice was 5.4, while for the test mice, the value continued to fall, to a level as far as 1.1.

TABLE 2

The effect of ZD 1839 on proliferation (Ki67 LI) in oestrogen stimulated normal breast epithelium

| Median Ki67 Labelling Index | Day 0 | Day 14 | Day 21 Control | Day 21 ZD1839 | Day 28 Control | Day 28 ZD1839 |
|---|---|---|---|---|---|---|
| Estrogen stimulated normal breast | 4.1 (3.2-5.3) | 2.6 (2.1-4) | 6.5 (5-8.6) | 1.4*** (0.8-1.9) | 5.4 (4.6-6.1) | 1.1*** (0.9-1.6) |

Numbers in parenthesis represent interquartile ranges
*p < 0.05, p < 0.01, *p < 0.001 vs control

EXAMPLE 4

Again using the method of Example 1, the effect of ZD1839 on apoptosis (AI) in oestrogen stimulated normal breast epithelium was measured. The results are shown in Table 3.

In the normal breast epithelium, on day 0, the date of implantation into a mouse, the AI value was 0.3 and reduced to 0.2 on the 14th day. Control mice were then treated with oestrogen alone, while the test mice were treated with both oestrogen and ZD1839. The amount of oestrogen administered corresponded to a premenopausal level. After 21 days, the AI value for the control mice was as high as 0.5, whereas for the test mice the value was even higher, at a value of 0.7. After 28 days, the AI value for the control mice was 0.6, while for the test mice, the value remained at a level of 0.7.

TABLE 3

The effect of ZD1839 on apoptosis (AI) in oestrogen stimulated normal breast epithelium

| Median Apoptotic Index | Day 0 | Day 14 | Day 21 Control | Day 21 ZD1839 | Day 28 Control | Day 28 ZD1839 |
|---|---|---|---|---|---|---|
| Oestrogen stimulated normal breast | 0.3 (0.19-0.3) | 0.2 (0.1-0.2) | 0.5 (0.45-0.65) | 0.7 (0.55-0.78) | 0.6 (0.45-0.66) | 0.7 (0.57-0.81) |

Numbers in parenthesis represent interquartile ranges
**p < 0.01 vs control

EXAMPLE 5

Using the same application regime as in Example 1, the effect of ZD1839 on progesterone receptor expression (PR LI) in oestrogen stimulated normal breast epithelium was measured (progesterone receptor increases the hormonal responsiveness of the cell). The results are shown in Table 4.

In the normal breast epithelium, on day 0, the date of implantation into a mouse, the PR LI value was 11.8 and reduced to 5.8 on the 14th day. Control mice were then treated with oestrogen alone, while the test mice were treated with both oestrogen and ZD1839. The amount of oestrogen administered corresponded to a premenopausal level. After 21 days, the PR LI value for the control mice rose to as high as 17.2, whereas for the test mice the value was only 10.4. Oestrogen induction of PR expression was therefore suppressed by ZD1839. Thus, the hormonal effects (normally mediated through the progesterone receptors) of the sex steroid progesterone and androgen are inhibited.

TABLE 4

The effect of ZD1839 on PR expression (PR LI) in oestrogen stimulated normal breast and epithelium

| Median PR LI (%) | Day 0 | Day 14 | Day 21 Control | Day 21 ZD1839 |
|---|---|---|---|---|
| Oestrogen stimulated normal breast | 11.8 (6.9-13.5) | 5.8 (4.5-7.7) | 17.2 (13.5-22.0) | *10.4 (8.9-13.1) |

Numbers in parenthesis represent interquartile ranges
**p < 0.001 vs control

From the above results, it can be seen that as stated hereinbefore, the inhibitory effect on constitutive growth and promotive effect on the death of normal breast cell tissue provides a method for inhibition of the transformation of normal cells into cancerous cells i.e. the basis for the chemopreventative treatment of women, particularly those at higher risk of developing malignant breast cancer.

Studies of normal breast epithelium show that hormone replacement therapy (HRT) increases expression of progesterone receptor (see Hargreaves et al, *Br. J Cancer*, (October 1998), 78(7), 945-949 and Hofscth et al, *J. Clin. Endocrinol. Metab.*, (December 1999), 84(12), 4559-4565) and combined HRT (oestrogen and progesterone) increases breast epithelial proliferation significantly more than does HRT with oestrogen alone (see Hofstch, Supra). Longer term combined HRT use has an increased breast cancer induction rate as compared with HRT with oestrogen alone (see Persson et al, *Cancer Causes Control*, (August 1999), 10(4), 253-260; Colditz, *J. Womens Health*, (April 1999), 8(3), 347-357; and Magnusson et al, *Int. J. Cancer*, (5 May 1999), 81(3), 339-344). By inhibiting the induction of progesterone receptor, progesterone cannot exert its effects and the frequency of breast cancer development is reduced.

In addition, the inhibiting effect upon oestrogen stimulated normal breast tissue indicates that EGFR tyrosine kinase inhibitor will work alone even in the presence of high levels of oestrogen: i.e. to provide chemoprevention in premenopausal women.

Thus, EGFR-TK inhibition offers a novel approach to the treatment and prevention of cancer regardless of ER status and provides a potential new chemopreventative approach, especially in high risk breast cancer families.

The invention claimed is:

1. A method of inhibiting the progression of breast cancer from a non-invasive in-situ cancer to an invasive cancer in a patient, wherein the method comprises administering to a patient in need thereof, prior to the onset of invasive cancer therein, an effective amount of N-(3-chloro-4-fluorophenyl)-7-methoxy-6-(3-morpholinopropoxy)quinazoline-4-amine (ZD1839); and wherein the ZD 1839 simultaneously decreases proliferation and increases apoptosis of the patient's non-invasive in-situ cancer cells.

2. The method of claim 1, which further comprises administering to the patient an antiestrogen.

3. The method of claim 2, wherein the N-(3-chloro-4-fluorophenyl)-7-methoxy-6-(3-morpholino propoxy)quinazoline-4-amine (ZD1839) and the antiestrogen are administered simultaneously.

4. The method of claim 2, wherein the N-(3-chloro-4-fluorophenyl)-7-methoxy-6-(3-morpholino propoxy)quinazoline-4-amine (ZD1839) and the antiestrogen are administered separately.

5. The method according to claim 2, wherein the antiestrogen is selected from the group consisting of tamoxifen, fulvestrant, raloxifene and mixtures thereof.

* * * * *